(12) United States Patent
Rheinheimer et al.

(10) Patent No.: US 11,385,103 B2
(45) Date of Patent: Jul. 12, 2022

(54) WATER COLOR PIGMENT SOLUTIONS FOR USE WITH REFLECTANCE-BASED DIAGNOSTIC ANALYZERS

(71) Applicant: Siemens Healthcare Diagnostics Inc., Tarrytown, NY (US)

(72) Inventors: Gary W. Rheinheimer, Goshen, IN (US); Chris T. Zimmerle, Goshen, IN (US); Linda Anderson-Mauser, Elkhart, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 17/193,185

(22) Filed: Mar. 5, 2021

(65) Prior Publication Data

US 2021/0199506 A1    Jul. 1, 2021

Related U.S. Application Data (62) Division of application No. 16/067,695, filed as application No. PCT/US2017/012288 on Jan. 5, 2017, now Pat. No. 10,969,279.

(60) Provisional application No. 62/276,559, filed on Jan. 8, 2016.

(51) Int. Cl.
| | |
|---|---|
| G01J 3/46 | (2006.01) |
| G01J 3/52 | (2006.01) |
| C09B 67/20 | (2006.01) |
| C09B 67/44 | (2006.01) |
| C09B 67/46 | (2006.01) |
| G01N 33/52 | (2006.01) |

(52) U.S. Cl.
CPC .......... *G01J 3/524* (2013.01); *C09B 67/0066* (2013.01); *C09B 67/0083* (2013.01); *C09B 67/0084* (2013.01); *G01N 33/52* (2013.01)

(58) Field of Classification Search
CPC ........ G01J 3/46; G01J 3/50; G01J 3/02; G01J 3/524; G01J 3/51
USPC .......................................... 356/402
See application file for complete search history.

(56) References Cited

U.S. PATENT DOCUMENTS

| | | | |
|---|---|---|---|
| 4,084,983 | A | 4/1978 | Bernhard et al. |
| 2005/0043436 | A1 | 2/2005 | Kwan et al. |
| 2007/0196095 | A1 | 8/2007 | Perala et al. |
| 2012/0013779 | A1 | 1/2012 | Hattery et al. |
| 2012/0077278 | A1 | 3/2012 | Roelant et al. |
| 2013/0002531 | A1 | 1/2013 | Krahenbuhl et al. |
| 2014/0127619 | A1 | 5/2014 | Farrugia et al. |
| 2017/0148189 | A1 | 5/2017 | Li |

FOREIGN PATENT DOCUMENTS

| | | |
|---|---|---|
| CN | 103091316 A | 5/2013 |
| EP | 0388932 A2 | 9/1990 |
| EP | 0491131 A1 | 6/1992 |
| JP | 3046416 U | 3/1998 |

OTHER PUBLICATIONS

International Search Report and Written Opinion of International Application No. PCT/US2017/012288 dated Mar. 17, 2017.

(Continued)

*Primary Examiner* — Md M Rahman
(74) *Attorney, Agent, or Firm* — Dunlap Codding, P.C.

(57) ABSTRACT

Provided herein are color charts and water color pigment solutions useful, for example, in the calibration of reflectance-based diagnostic analyzers.

11 Claims, 2 Drawing Sheets

(56) References Cited

OTHER PUBLICATIONS

European Search Report and Search Opinion of European Application No. 17736306.6 dated Dec. 14, 2018.
U.S. Appl. No. 16/067,695; Office Action dated Apr. 17, 2020.
U.S. Appl. No. 16/067,695; Response to Office Action dated Jun. 16, 2020.
U.S. Appl. No. 16/067,695; Office Action dated Jul. 1, 2020.
U.S. Appl. No. 16/067,695; Response to Office Action dated Oct. 23, 2020.
U.S. Appl. No. 16/067,695; Notice of Allowance dated Dec. 7, 2020.

WATER COLOR PIGMENT SOLUTIONS FOR USE WITH REFLECTANCE-BASED DIAGNOSTIC ANALYZERS

CROSS REFERENCE TO RELATED APPLICATIONS/INCORPORATION BY REFERENCE STATEMENT

This application is a divisional of U.S. Ser. No. 16/067,695, filed Jan. 5, 2017; which is a US National Stage Application under 35 USC § 371 of International Application No. PCT/US2017/12288, filed Jan. 5, 2017; which claims priority to U.S. Provisional Application No. 62/276,559, filed Jan. 8, 2016, the disclosure of which is hereby incorporated by reference in its entirety.

TECHNICAL FIELD

Provided herein are color charts and water color pigment solutions useful, for example, in the calibration of a reflectance-based diagnostic analyzer.

BACKGROUND

The diagnostic evaluation of sample liquids (such as, but not limited to, whole blood, urine, saliva, and plasma) often involves dispensing a portion of the sample liquid onto a reagent pad and then observing the changes to the reagent pad (changes in color, for example). Diagnostic analyzers, such as the CLINITEK Novus® urine analyzer, can be used to inspect reagent pads for color changes via reflectance-based measurement(s) (as opposed to an absorbance based measurement). The CLINITEK Novus® urine analyzer reports values for the following results: yellow, dark yellow, orange, red, green, and other.

Urine can have a variety of colors as a result of a patient's clinical state or the elimination of drugs from the body. Use of a diagnostic analyzer to determine these colors on a reagent pad can have a significant impact on the patient's diagnosis. It is therefore important to evaluate the color output of these instruments for accuracy.

BRIEF DESCRIPTION OF THE DRAWINGS

The following detailed description is further understood when read in conjunction with the appended drawings. For the purpose of illustrating the disclosed color charts, water color pigment solutions, methods, and kits there are shown in the drawings exemplary embodiments of the color charts, water color pigment solutions, methods, and kits; however, the color charts, water color pigment solutions, methods, and kits is not limited to the specific embodiments disclosed. In the drawings.

DETAILED DESCRIPTION

Provided herein are color charts comprising a surface material having one or more color swatches, wherein the color swatches comprise one or more layers of a dried water color pigment solution, wherein the water color pigment solution contains color pigment molecules. Kits comprising the color charts are also provided.

Also disclosed are water color pigment solutions comprising a suspension of one or more water color pigments and urine or a solution that mimics urine. Kits comprising the water color pigment solutions are also provided.

Methods of calibrating a reflectance-based diagnostic analyzer are also provided, wherein the methods comprise: inserting any of the herein disclosed color charts or water color pigment solutions into the reflectance-based diagnostic analyzer, wherein the color chart or the water color pigment solutions have a known color; obtaining reflectance values for the color chart or the water color pigment solutions; and if the obtained reflectance values do not correspond to the known color of the color chart or the water color pigment solutions, calibrating the analyzer such that the reflectance values correspond to the known color of the color chart or the water color pigment solutions.

The disclosed color charts, water color pigment solutions, methods, and kits may be understood more readily by reference to the following detailed description taken in connection with the accompanying figures, which form a part of this disclosure. It is to be understood that the disclosed color charts, water color pigment solutions, methods, and kits are not limited to the specific color charts, water color pigment solutions, methods, and kits described and/or shown herein, and that the terminology used herein is for the purpose of describing particular embodiments by way of example only and is not intended to be limiting of the claimed color charts, water color pigment solutions, methods, and kits.

Unless specifically stated otherwise, any description as to a possible mechanism or mode of action or reason for improvement is meant to be illustrative only, and the disclosed color charts, water color pigment solutions, methods, and kits are not to be constrained by the correctness or incorrectness of any such suggested mechanism or mode of action or reason for improvement.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the present disclosure. Where a range of numerical values is stated herein as being less than a stated value, the range is nevertheless bounded on its lower end by a non-zero value. It is not intended that the scope of the invention be limited to the specific values recited when defining a range. All ranges are inclusive and combinable.

When values are expressed as approximations, by use of the antecedent "about," it will be understood that the particular value forms another embodiment. Reference to a particular numerical value includes at least that particular value, unless the context clearly dictates otherwise.

It is to be appreciated that certain features of the disclosed color charts, water color pigment solutions, methods, and kits which are, for clarity, described herein in the context of separate embodiments, may also be provided in combination in a single embodiment. Conversely, various features of the disclosed color charts, water color pigment solutions, methods, and kits that are, for brevity, described in the context of a single embodiment, may also be provided separately or in any subcombination.

Any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

The term "about" is used to encompass variations of ±10% or less, variations of ±5% or less, variations of ±1% or less, variations of ±0.5% or less, or variations of ±0.1% or less from the specified value.

The term "comprising" is intended to include examples encompassed by the terms "consisting essentially of" and "consisting of"; similarly, the term "consisting essentially of" is intended to include examples encompassed by the term "consisting of."

Unless expressly stated to the contrary, "or" refers to an inclusive "or" and not to an exclusive "or." For example, a condition A or B is satisfied by anyone of the following: A is true (or present) and B is false (or not present); A is false (or not present) and B is true (or present); and both A and B are true (or present). An inclusive "or" may be understood as being the equivalent to at least one of condition A or B.

The following abbreviations are used herein: Dark Yellow (D. Yellow); Middlebury Street Plant General Method (MSPGM); Online Document Library—Middlebury Street (ODL); National Institute of Standards and Technology (NIST).

Color Charts and Water Color Pigment Solutions

It is important to evaluate the color output of diagnostic instruments to ensure accuracy. This evaluation can be done with the use of color solutions which are typically made from color dyes. For consistent results, this color solution should be compared to National Institute of Standards and Technology ("NIST") traceable standards yielding color values. Because color dye solutions cannot be accurately measured using reflectance-based systems, NIST traceable instruments that give absorbance values are used. Making an accurate, direct comparison between the absorbance values of the color dye to an NIST standard, however, is extremely difficult. Color output can be measured using absorbance-based methods, but the resulting absorbance values do not correctly correlate to reflectance readings (obtained by, for example, a diagnostic analyzer). Accordingly, color dyes are inadequate for evaluating the color output values from reflectance instruments.

Color reference charts, another reference tool, can be created by printing ink. For example, various colors can be printed on a paper substrate which can then be evaluated by the reflectance-based diagnostic analyzer. Getting accurate colors using ink, however, is difficult. The intensity of color ink is determined by mixing primary colors and white prior to applying the ink to a substrate, which makes it extremely difficult to precisely control the intensity (or hue) of the ink once it is on the substrate and dry. Moreover, ink sits on top of the substrate to which it is applied rather than being absorbed into the substrate.

The disclosed color charts and water color pigment solutions offer advantages over prior reference charts and color solutions. For example, water color pigments are employed in the disclosed color charts and water color pigment solutions to make a standardized color chart/solution that can be analyzed with an independent NIST traceable reflective color instrument.

Disclosed herein are color charts comprising a surface material having one or more color swatches, wherein the color swatches comprise one or more layers of a dried water color pigment solution, wherein the water color pigment solution contains color pigment molecules.

The hue of each color swatch in the color chart is related to the number of layers of the dried water color pigment solution present on the swatch. A color swatch having multiple layers of a dried water color pigment solution can have a darker hue compared to a color swatch having fewer layers of the dried water color pigment solution. For example, a color swatch having 5 layers of dried water color pigment solution will be darker than a color swatch having 1 layer of the same dried water color pigment solution.

The disclosed color charts can comprise one or more color sections, wherein the one or more color swatches are arranged in the one or more color sections. In some embodiments, for example, the one or more color sections can comprise a red color section, an orange color section, a yellow color section, a green color section, or any combination thereof. Each of these color sections can be further subdivided based upon the intensity of the color. For example, in some embodiments, the yellow color section can comprise a dark yellow color section, a light yellow color section, or both a dark yellow color section and a light yellow color section.

The color sections can comprise the following hues:
a. the red color section can comprise a hue from about 347.1 to about 360.0 or from about 0.0 to about 20.0;
b. the orange color section can comprise a hue from about 24.1 to about 36.7;
c. the yellow color section can comprise a hue from about 38.4 to about 57.0;
d. the green color section can comprise a hue from about 74.5 to about 120.0; or
e. any combination of a-d.

The color of the one or more color swatches can correlate with a color of one or more water color pigment solutions. Exemplary water color pigment solutions are provided herein.

The color swatches comprise a dried water color pigment solution, which, prior to being dried, can comprise a suspension of one or more water color pigments. Thus, the color swatches comprise color pigment molecules.

Exemplary water color pigments include orange water color pigments, brilliant red water color pigments, medium yellow water color pigments, cobalt blue water color pigments, raw umber water color pigments, sap green water color pigments, or any combination thereof. In some embodiments, the one or more water color pigments can comprise orange, brilliant red, medium yellow, cobalt blue, raw umber, sap green, or any combination thereof.

The color swatches can be created from water color pigments of the same color or from a mixture of water color pigments of different colors. In some embodiments, the one or more water color pigments comprises a combination of:

a) brilliant red and cobalt blue;
b) brilliant red and orange;
c) orange and medium yellow;
d) medium yellow and sap green; or
e) sap green and cobalt blue.

The color swatches can be prepared from any of the water color pigment solutions disclosed herein, which can be applied to a reagent-less pad or a sheet of paper (such as water color paper) and allowed to dry. As opposed to applying a dye, or printing colored ink, onto a surface material, application of the disclosed water color pigment solutions onto the surface material will result in a layer of color pigment molecules on the surface material. Application of additional layers of the water color pigment solution will, upon drying, result in a darker hue. These color intensities can be used to mimic urine concentrations. Use of water color pigment solutions results in a more accurate color intensity, or hue, that can be traced to an NIST standard and evaluated by the reflectance-based diagnostic analyzer.

Figure 1:
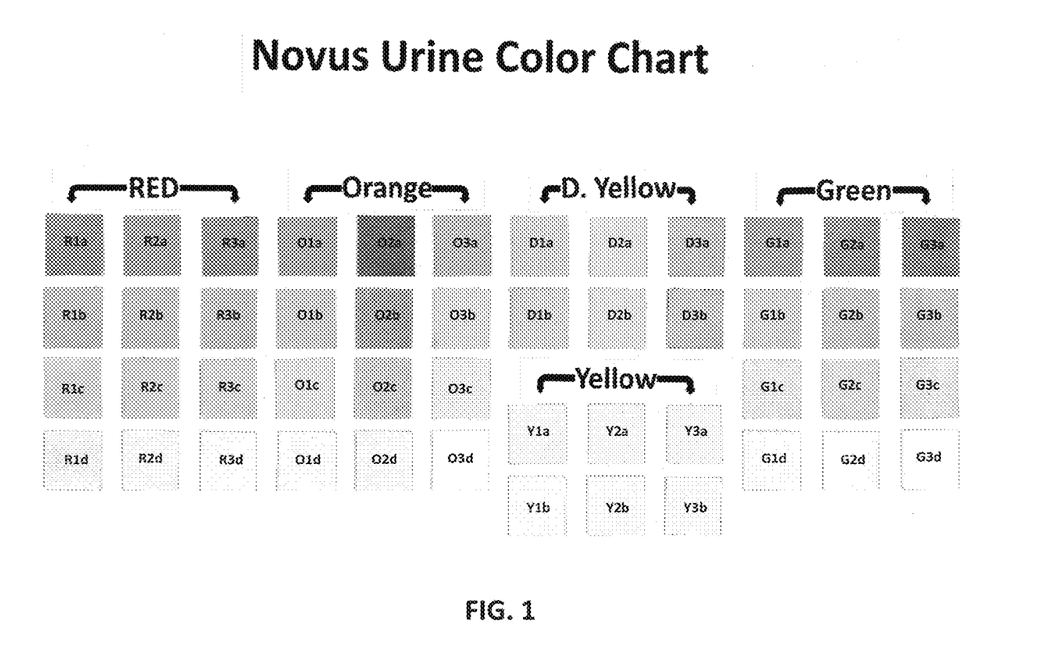
FIG. 1 illustrates an exemplary color chart.

An exemplary color chart is shown in FIG. 1. As shown in the figure, the color chart can comprise a Red, Orange, Dark Yellow (D. Yellow), Yellow, and Green color section, each color section having one or more color swatches. The individual color swatches are labeled using the following format: color—red (R), orange (O), d. yellow (D), yellow (Y), and green (G); column within each color section (1, 2, 3, etc.); and row within each color section (a, b, c, d, etc.). The intensity of the color swatch can be related to the number of layers of the dried water color pigment solution present on the swatch. For example, for each column of color swatches (R1$a$, R2$a$, R3$a$, for example) the swatches in row "a" have more layers of the dried water color pigment solution compared to the swatches in rows "b," "c," and "d." Thus, the hue of the "a" swatches is darker than that of the other rows. The color sections can also comprise color swatches made from dried water color pigment solutions of different hues. In the figure, for example, the color swatches in the column labeled "1," are made from a water color pigment solution having a different hue than the color swatches in the column labeled "2."

Also provided are water color pigment solutions comprising a suspension of one or more water color pigments. The one or more water color pigment solutions can be suspended in water, urine, or a solution that mimics urine, such as water comprising an appropriate amount of salt to mimic the isotonic strength of urine.

The water color pigment solutions can be prepared by weighing the appropriate amount of water color pigment and combining the water color pigment with the appropriate solution. For example, water color pigments can be measured at a predetermined weight on an analytical balance, transferred to a beaker, and diluted with a specific volume of urine or purified water. In embodiments wherein the water color pigments are diluted in purified water, salt (such as NaCl) can be added to mimic the isotonic strength of normal urine. Many water color pigment solutions can be developed due to the variety of available color pigments. The pigments can be combined and the concentration altered to achieve an even greater array of colors as exemplified in the Examples herein.

The one or more water color pigments can comprise orange, brilliant red, medium yellow, cobalt blue, raw umber, sap green, or any combination thereof. The water color pigment solutions can be created from water color pigments of the same color. In some embodiments, the water color pigments can comprise:

a) Orange at a concentration of about 4 mg/ml to about 5 mg/ml;
b) Brilliant red at a concentration of about 4 mg/ml to about 5 mg/ml;
c) Medium yellow at a concentration of about 7 mg/ml to about 8 mg/ml;
d) Cobalt blue at a concentration of about 8 mg/ml to about 9 mg/ml;
e) Raw umber at a concentration of about 6 mg/ml to about 7 mg/ml; or
f) Sap green at a concentration of about 17 mg/ml to about 18 mg/ml.

The water color pigment solutions can be created from a mixture of water color pigments of different colors. In some embodiments, the one or more water color pigments can comprise a combination of:

a) brilliant red and cobalt blue;
b) brilliant red and orange;
c) orange and medium yellow;
d) medium yellow and sap green; or
e) sap green and cobalt blue.

Exemplary mixtures of water color pigments comprise:
a) about 6.5 parts brilliant red to about 1 part cobalt blue;
b) about 1 part brilliant red to about 2 parts orange;
c) about 2 parts orange to about 1 part medium yellow;
d) about 14 parts medium yellow to about 1 part orange;
e) about 4 parts medium yellow to about 1 part sap green;
f) about 1 part medium yellow to about 2 parts sap green;
g) about 6.5 parts sap green to about 1 part cobalt blue; or
h) about 2 parts sap green to about 1 part cobalt blue.

The mixtures of water color pigments in a)-h) above can be further diluted. In some embodiments, the mixtures can be further diluted with urine. In some embodiments, the mixtures can be further diluted with water. In some embodiments, the mixtures can be further diluted with a solution configured to mimic urine, such as water comprising an appropriate amount of salt to mimic the isotonic strength of urine. Exemplary dilutions, which can be made with urine, water, or the urine mimic include:

the water color pigment of a) further diluted 1:4;
the water color pigment of b) further diluted 1:30;
the water color pigment of c) further diluted 1:4 or 1:10;
the water color pigment of d) further diluted 1:4 or 1:15;
the water color pigment of e) further diluted 1:4 or 1:13;
the water color pigment of g) further diluted 1:10; or
the water color pigment of h) further diluted 1:9.

The water color pigment solutions can further comprising a preservative. Suitable preservatives comprise, for example, sodium azide.

Any of the above disclosed water color pigment solutions can be used to create the herein disclosed color charts. For example, the color pigment solutions can be layered onto a water color paper or reagent-less pad. By increasing the number of layers of water color pigment solutions, the color intensities can be precisely controlled.

The disclosed water color pigment solutions can be used by reflectance-based instruments to calibrate the sensors and correct their color value readings.

Methods of Calibrating a Reflectance-Based Diagnostic Analyzer

Provided herein are methods of calibrating a reflectance-based diagnostic analyzer comprising:

inserting any of the disclosed color charts or any of the disclosed water color pigment solutions into the reflectance-based diagnostic analyzer, wherein the color chart or the water color pigment solutions have a known color;

obtaining reflectance values for the color chart or the water color pigment solutions; and if the obtained reflectance values do not correspond to the known color of the color chart or the water color pigment solutions, calibrating the analyzer such that the reflectance values correspond to the known color of the color chart or the water color pigment solutions.

In some embodiments, the reflectance-based diagnostic analyzer can be a CLINITEK Novus® instrument. In some embodiments, the reflectance-based diagnostic analyzer can comprise a portable diagnostic analyzer. One example of a portable diagnostic analyzer is a digital camera coupled to a processor—such as those found in a smart phone, tablet, or other hand held diagnostic analyzer (collectively "portable diagnostic analyzers"). An illustrative inventive method of using a portable diagnostic analyzer includes the use of the color charts herein as a reference to improve accuracy/calibration of near patient or at home testing. Another method includes teaching a patient to use a portable diagnostic analyzer and any of the disclosed color charts as a reference to improve accuracy/calibration of near patient or at home testing.

Kits

Further provided are kits comprising any of the herein disclosed color charts or any of the herein disclosed water color pigment solutions and instructions for using the color charts or water color pigment solutions. In some embodiments, the kits comprise any of the herein disclosed color charts and instructions for using the color charts. In some embodiments, the kits comprise any of the herein disclosed water color pigment solutions and instructions for using the water color pigment solutions.

In some embodiments, the instructions explain to a user of the kit how to calibrate a reflectance-based diagnostic analyzer.

EXAMPLES

The following examples are provided to further describe some of the embodiments disclosed herein. The examples are intended to illustrate, not to limit, the disclosed embodiments.

Experimental design: Twenty-one (21) contrived urine color solutions were developed using water color pigments. These solutions correlate to a CieLab DE instrument which was calibrated to the International Committee for Illumination (CIE) publication No. 15.2. A color chart for matching to Novus color blocks was also developed from contrived color solutions.

The contrived urine color solutions were evaluated with one (1) replicate on each of three (3) CLINITEK Novus® instruments (S/N P100046, 5001165, and 5001109) using a single lot of CLINITEK Novus® 10-Way reagents (lot K117123). Five (5) visual readers evaluated each sample comparing the color of the sample to a color chart.

Development of Color Solutions: Prior art color solutions do not have the variation needed to evaluate the range of the CLINITEK Novus® color blocks. Thus, new color solutions were developed using water color pigments, of which seventeen (17) individual pigments were selected for processing. During initial development, quantities of each pigment paste were diluted with polished water, and each solution was evaluated with the CLINITEK Novus® to determine the hue value (data not shown). The pigments in Table 1 and Base Solutions generated from the pigments (Table 2) were selected for further evaluation based on the CLINITEK Novus® hue value and color block ranges.

TABLE 1

Water Color Pigments Materials

| Color | Source | Part No. | Used in Solution No. |
|---|---|---|---|
| Orange | Reeves | 8404150 | 5-Orange |
| Brilliant Red | Reeves | 8404230 | 6-RedBril |
| Medium Yellow | Reeves | 8404120 | 8-YelMed |
| Cobalt Blue | Grumbacher | 1417335065 | 13-BluCob |
| Raw Umber | Grumbacher | 1417335093 | 15-Umber |
| Sap Green | Reeves | 8404428 | 16-GreSap |

The six (6) selected pigments were used to generate the Base Solutions, as shown in Table 2. Due to the small tubes in which the pigments come, a small spatula was needed to transfer the pigment from the tube to the diluting container. The amount of pigment for each color was determined by pre-weighing the spatula on an analytical balance and then weighing the spatula with the pigment. To generate the Base Solutions, the appropriate amount of pigment was combined with a solution containing urine having normal analyte levels (as measured on a Multistix 10SG urine strip) and sodium azide. A total of 940 mL was needed to make the final solutions; 628 mL for base solutions and 312 for dilutions. Accordingly, 1500 mL of negative urine was collected, and to this 300 mg of sodium azide was added as a preservative. The "Volume Needed" was based on what was required to make the Base Solutions, Target Solutions, and the Target Solution dilutions using a 40 mL final volume. An additional 10 mL were added to allow for solution preparation. The mg/mL was based on the initial development of the color solutions.

TABLE 2

Base Solution Preparation Amounts

| Base Color | Volume Needed (ml) | Volume + 10 mL (ml) | mg/mL | Pigment (mg) |
|---|---|---|---|---|
| 5-Orange | 70 | 80 | 4.59 | 365.3 |
| 6-RedBril | 106 | 116 | 4.66 | 541.8 |
| 8-YelMed | 202 | 212 | 7.07 | 1496.5 |
| 13-BluCob | 28 | 38 | 8.73 | 330.7 |
| 15-Umber | 55 | 65 | 6.50 | 422.5 |
| 16-GreSap | 108 | 118 | 17.02 | 2005.0 |

Figure 2:
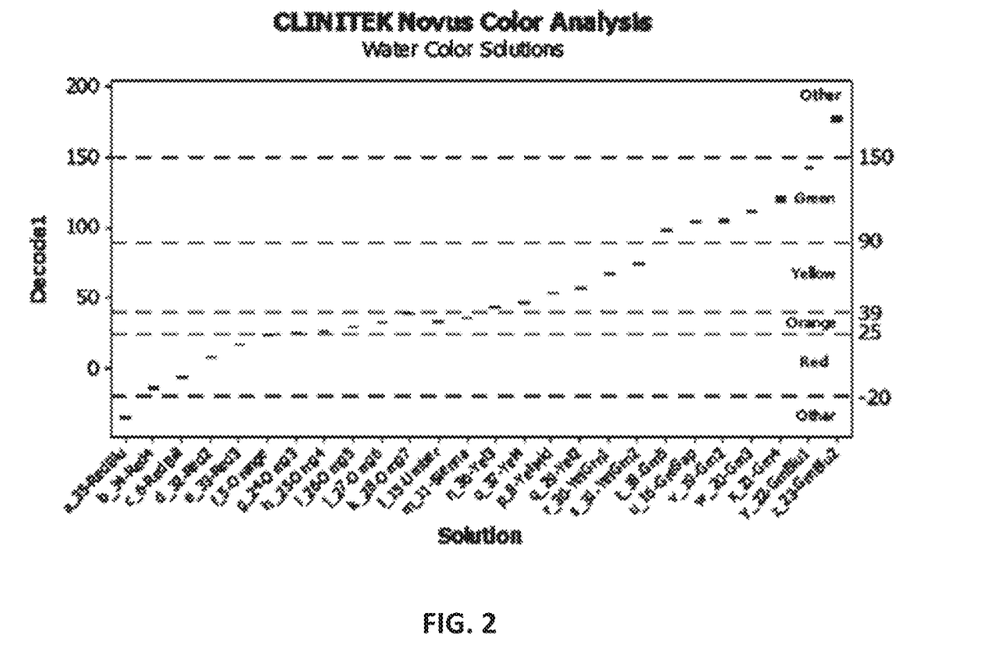
FIG. 2 illustrates the distribution of various CLINITEK Novus® Water color pigment solutions across the CLINITEK Novus® hue range. A total of 26 (6 Base Solutions and 20 novel solutions) were analyzed on a single CLINITEK Novus® to determine the hue values.

Twenty (20) Test Solutions were prepared using various combinations of the Base Solutions (data not shown). The Test Solutions used the Base Solutions in different ratios to obtain a variety of colors across the CLINITEK Novus® hue range. The twenty (20) additional solutions, along with six (6) of the Base Solutions, were analyzed on a single CLINITEK Novus® to determine the hue values. This data was sorted and placed into the graph in FIG. 2, which shows the distribution across the CLINITEK Novus® hue range. Solution 13 Cobalt Blue was not tested and only used for mixing purposes.

Based on the above analysis, 11 combinations were selected as Target Solutions. Three (3) solutions were designated for each of the following CLINITEK Novus® color blocks: Red, Yellow, and Green, along with two for the Orange color block (Table 3). The Target Solutions were prepared according to Table 3, which lists the Base Solutions used for each target along with the percent volume for that solution. An additional 10% of volume was added to allow for processing.

TABLE 3

Target Solution Preparation Volumes

| Target Solution | Base Solution | Percent Volume | Total (mL) | Total + 10% (ml) | Color Block |
|---|---|---|---|---|---|
| 34-Red4 | 6 | 86.67 | 43.33 | 47.67 | Red |
|  | 13 | 13.33 | 6.67 | 7.33 |  |
| 6-RedBril | 6 | 100.00 | 40.00 | 44.00 |  |

TABLE 3-continued

Target Solution Preparation Volumes

| Target Solution | Base Solution | Percent Volume | Total (mL) | Total + 10% (ml) | Color Block |
|---|---|---|---|---|---|
| 33-Red3 | 6 | 33.33 | 13.33 | 14.67 |  |
|  | 5 | 66.67 | 26.67 | 29.33 |  |
| 25-Orng4 | 5 | 66.67 | 33.33 | 36.67 | Orange |
|  | 8 | 33.33 | 16.67 | 18.33 |  |
| 15-Umber | 15 | 100.00 | 50.00 | 55.00 |  |
| 36-Yel3 | 8 | 93.33 | 46.67 | 51.33 | Dark Yellow |
|  | 5 | 6.67 | 3.33 | 3.67 |  |
| 8-YelMed | 8 | 100.00 | 66.67 | 73.33 |  |
| 30-YelGrn1 | 8 | 80.00 | 40.00 | 44.00 |  |
|  | 16 | 20.00 | 10.00 | 11.00 |  |
| 38-Grn5 | 8 | 33.33 | 13.33 | 14.67 | Green |
|  | 16 | 66.67 | 26.67 | 29.33 |  |
| 20-Grn3 | 16 | 86.67 | 34.67 | 38.13 |  |
|  | 13 | 13.33 | 5.33 | 5.87 |  |
| 22-GrnBlu1 | 16 | 66.67 | 26.67 | 29.33 |  |
|  | 13 | 33.33 | 13.33 | 14.67 |  |

The 11 Target Solutions were diluted in varying amounts depending on the solution and its concentration (a total of 15 dilutions ranging from 3/4 to 1/80 were used; however, not all Target Solutions were diluted in the same ratios). 65 diluted solutions were generated from the 11 Target Solutions. The dilutions were analyzed on a CLINITEK Novus® to determine the hue value (data not shown). Using both the compiled CLINITEK Novus® data and visual analysis, 21 Final Color Solutions (Table 4) were selected.

The Final Color Solutions were designated in terms of dilutions. The column headings list the dilution number along with the ratio of target solution to urine. Dilution 1 was the undiluted target solution. After the diluting process was complete, solutions 36-Yel3 Dil. 10, 8-YelMed Dil. 8 & Dil. 10 and 30-YelGrn1 Dil. 9 from Table 4 were further diluted 1:3 with water to obtain the final solutions for the Yellow color block (water was used for this dilution because the negative urine color added to the solution intensity). The Final Color Solutions were refrigerated in capped containers.

TABLE 4

Final Color Solutions

| Target Soln | Soln | Dil. 1 1:1 | Dil. 3 2:3 | Dil. 6 1:4 | Dil. 8 1:10 | Dil. 9 1:13 | Dil. 10 1:15 | Dil. 12 1:9 | Dil. 13 1:30 |
|---|---|---|---|---|---|---|---|---|---|
| 34-Red4 | Target | 40.0 | — | 10.0 | — | — | — | — | — |
|  | Urine | 0.0 | — | 30.0 | — | — | — | — | — |
| 6-RedBril | Target | 40.0 | — | — | — | — | 2.667 | — | — |
|  | Urine | 0.0 | — | — | — | — | 37.333 | — | — |
| 33-Red3 | Target | — | — | — | — | — | — | — | 1.333 |
|  | Urine | — | — | — | — | — | — | — | 38.667 |
| 25-Orng4 | Target | — | — | 10.0 | 4.0 | — | — | — | — |
|  | Urine | — | — | 30.0 | 36.0 | — | — | — | — |
| 15-Umber | Target | — | — | 10.0 | — | — | — | — | — |
|  | Urine | — | — | 30.0 | — | — | — | — | — |
| 36-Yel3 | Target | 40.0 | — | 10.0 | — | — | 2.667 | — | — |
|  | Urine | 0.0 | — | 30.0 | — | — | 37.333 | — | — |
| 8-YelMed | Target | 40.0 | 26.667 | — | 4.0 | — | 2.667 | — | — |
|  | Urine | 0.0 | 13.333 | — | 36.0 | — | 37.333 | — | — |
| 30-YelGrn1 | Target | — | — | 10.0 | — | 3.077 | — | — | — |
|  | Urine | — | — | 30.0 | — | 36.923 | — | — | — |
| 38-Grn5 | Target | 40.0 | — | — | — | — | — | — | — |
|  | Urine | 0.0 | — | — | — | — | — | — | — |
| 20-Grn3 | Target | 40.0 | — | — | 4.0 | — | — | — | — |
|  | Urine | 0.0 | — | — | 36.0 | — | — | — | — |
| 22-GrnBlu1 | Target | — | — | — | — | — | — | 4.444 | — |
|  | Urine | — | — | — | — | — | — | 35.556 | — |

Color Chart Development: There are no hard color standards (i.e. paper-based or non-liquid) available for CLINITEK Novus® color solutions. Therefore, a color chart was developed using the same material that the Final Color Solutions were made from. To create the color chart, a series of one (1) inch squares were penciled onto cold press artist paper in a 6×10 pattern. Using a ½ inch width paint brush, some of the Target Solutions were systematically applied to the squares in a series of increasing coating applications, the greater the number of coatings the more intense the color. There were 4 squares for the Red, Orange, and Green target colors. 5 squares were used for the yellow target color. The extra square was used to help differentiate between Dark Yellow and Yellow. Table 5 lists the number of coatings needed to obtain the desired color intensities.

TABLE 5

Color Chart Swatch Coatings

| Target Solution | Square 1 | Square 2 | Square 3 | Square 4 | Square 5 |
|---|---|---|---|---|---|
| 34-Red4 | 1 | 5 | 9 | 16 | — |
| 6-RedBril | 1 | 5 | 9 | 16 | — |
| 33-Red3 | 1 | 5 | 9 | 16 | — |
| 25-Orng4 | 1 | 5 | 9 | 16 | — |
| 15-Umber | 1 | 5 | 9 | 16 | — |
| 28- Orng7 | 1 | 5 | 9 | 16 | — |
| 36-Yel3 | 2 | 4 | 9 | 15 | 16 |
| 8-YelMed | 2 | 4 | 9 | 15 | 16 |
| 30-YelGrn1 | 2 | 4 | 9 | 15 | 16 |
| 38-Grn5 | 2 | 5 | 9 | 16 | — |

TABLE 5-continued

Color Chart Swatch Coatings

| Target Solution | Square 1 | Square 2 | Square 3 | Square 4 | Square 5 |
|---|---|---|---|---|---|
| 20-Grn3 | 2 | 5 | 9 | 16 | — |
| 22-GrnBlu1 | 2 | 5 | 9 | 16 | — |

The coated squares were cut into individual swatches, aligned, and attached to a cardboard backing. The cold press paper was pre-laminated with double sided adhesive before coating began so that the swatches could easily be attached to the chart. All swatches were used except for square 3 from the yellow Target Solutions (#36-Yel3, 8-YelMed & 30-Yel-Grn1). This enabled Yellow and Dark Yellow to be distinguished. Labels were made and attached to the chart. An exemplary color chart is shown in FIG. 1.

The chart was divided into 5 color sections and each section contained 3 columns of color swatches. The columns were further divided into rows of decreasing swatch color intensity.

The Mercury DataColor instrument (Serial Number 1007) was used to obtain CieLab data readings from each of the 48 swatches on the color chart (Tables 6 to 11). The CieLab readings were converted to HSV values. The CieLab data readings and HSV values are color space systems used to define colors and hues in numerical terms. The CLINITEK Novus® uses the HSV system. To compare the Novus to the color swatches, the Mercury DataColor was employed, which used the CieLab color space system. This data was converted to HSV values. For each of Tables 6 to 11 the following applies: L, a, b, c, h and H, S, V represented 2 types of color space indicators. "L" indicates lightness; "a" indicates the red/green component; "b" indicates the yellow/blue component; "c" and "h" indicate the other parts of the system; "H" indicates Hue; "S" indicates the saturation component; and "V" indicates the value of lightness.

TABLE 6

Color Chart DataColor Instrument Readings: Red Color Block

| | | Block | | | | | | | |
|---|---|---|---|---|---|---|---|---|---|
| | | Red Column 1 ("R1") | | | | Red Column 2 ("R2") | | | |
| | | Row | | | | | | | |
| | | a | b | c | d | a | b | c | d |
| DataColor | L | 64.33 | 75.80 | 83.30 | 89.15 | 70.34 | 77.99 | 83.13 | 90.88 |
| | a | 28.58 | 20.13 | 12.59 | 5.78 | 37.65 | 25.85 | 17.60 | 4.58 |
| | b | 3.11 | 3.28 | 3.91 | 4.61 | 12.54 | 8.32 | 6.53 | 5.63 |
| | c | 28.75 | 20.39 | 13.19 | 7.39 | 39.68 | 27.16 | 18.77 | 7.26 |
| | h | 6.20 | 9.26 | 17.25 | 38.55 | 18.42 | 17.84 | 20.34 | 50.88 |
| Converted | H | 347.1 | 350.8 | 358.3 | 12.5 | 355.7 | 356.6 | 0.0 | 17.5 |
| | S | 0.337 | 0.230 | 0.150 | 0.099 | 0.404 | 0.284 | 0.202 | 0.100 |
| | V | 0.809 | 0.884 | 0.919 | 0.938 | 0.950 | 0.959 | 0.959 | 0.951 |

TABLE 7

Color Chart DataColor Instrument Readings: Red and Orange Color Blocks

| | | Block | | | | | | | |
|---|---|---|---|---|---|---|---|---|---|
| | | Red Column 3 ("R3") | | | | Orange Column 1 ("O1") | | | |
| | | Row | | | | | | | |
| | | a | b | c | d | a | b | c | d |
| DataColor | L | 70.32 | 78.12 | 83.83 | 90.96 | 75.04 | 80.81 | 84.76 | 90.88 |
| | a | 39.56 | 26.55 | 18.83 | 4.30 | 33.84 | 22.72 | 15.17 | 4.36 |
| | b | 40.26 | 28.71 | 22.34 | 6.81 | 50.01 | 36.60 | 27.06 | 12.51 |
| | c | 56.45 | 39.10 | 29.22 | 10.71 | 60.38 | 43.08 | 31.02 | 13.24 |
| | h | 45.50 | 47.24 | 49.88 | 66.33 | 55.91 | 58.16 | 60.72 | 70.77 |
| Converted | H | 15.6 | 16.8 | 18.6 | 20.0 | 24.1 | 24.6 | 24.9 | 28.6 |
| | S | 0.604 | 0.445 | 0.341 | 0.110 | 0.635 | 0.477 | 0.367 | 0.170 |
| | V | 0.999 | 1.000 | 1.000 | 0.962 | 1.000 | 1.000 | 1.000 | 0.969 |

TABLE 8

Color Chart DataColor Instrument Readings: Orange Color Block

| | | Block | | | | | | | |
|---|---|---|---|---|---|---|---|---|---|
| | | Orange Column 2 ("O2") | | | | Orange Column 3 ("O3") | | | |
| | | Row | | | | | | | |
| | | a | b | c | d | a | b | c | d |
| DataColor | L | 56.40 | 70.43 | 78.90 | 89.23 | 79.82 | 84.94 | 87.73 | 92.04 |
| | a | 14.78 | 11.04 | 7.26 | 1.92 | 20.95 | 11.27 | 6.05 | 1.11 |

TABLE 8-continued

Color Chart DataColor Instrument Readings: Orange Color Block

|  |  | Block | | | | | | | |
|---|---|---|---|---|---|---|---|---|---|
|  |  | Orange Column 2 ("O2") | | | | Orange Column 3 ("O3") | | | |
|  |  | Row | | | | | | | |
|  |  | a | b | c | d | a | b | c | d |
|  | b | 33.62 | 31.63 | 26.11 | 14.25 | 53.46 | 37.80 | 27.65 | 12.39 |
|  | c | 36.72 | 33.50 | 27.10 | 14.38 | 57.42 | 39.45 | 28.30 | 12.44 |
|  | h | 66.27 | 70.76 | 74.45 | 82.31 | 68.61 | 73.39 | 77.65 | 84.89 |
| Converted | H | 28.5 | 30.3 | 32.3 | 35.7 | 31.9 | 32.1 | 36.4 | 36.7 |
|  | S | 0.563 | 0.451 | 0.348 | 0.175 | 0.618 | 0.446 | 0.418 | 0.146 |
|  | V | 0.691 | 0.824 | 0.886 | 0.938 | 1.000 | 1.000 | 1.000 | 0.958 |

TABLE 9

Color Chart DataColor Instrument Readings: Yellow Color Block

|  |  | Block | | | | | | | |
|---|---|---|---|---|---|---|---|---|---|
|  |  | D. Yellow Column 1 ("D1") | | Yellow Column 1 ("Y1") | | D. Yellow Column 2 ("D2") | | Yellow Column 2 ("Y2") | |
|  |  | Row | | | | | | | |
|  |  | a | b | c | d | a | b | c | d |
| DataColor | L | 84.37 | 84.90 | 90.38 | 91.80 | 88.53 | 88.79 | 91.51 | 92.11 |
|  | a | 9.84 | 9.08 | 0.75 | 0.02 | −1.76 | −1.87 | −2.14 | −1.66 |
|  | b | 54.81 | 52.59 | 24.71 | 17.35 | 57.67 | 56.50 | 24.92 | 18.35 |
|  | c | 55.69 | 53.36 | 24.72 | 17.35 | 57.70 | 56.53 | 25.01 | 18.42 |
|  | h | 79.83 | 80.21 | 88.26 | 89.94 | 91.75 | 91.90 | 94.90 | 95.17 |
| Converted | H | 38.4 | 38.3 | 40.3 | 40.9 | 46.6 | 46.7 | 45.7 | 44.3 |
|  | S | 0.587 | 0.563 | 0.267 | 0.191 | 0.567 | 0.555 | 0.254 | 0.188 |
|  | V | 1.000 | 1.000 | 0.970 | 0.961 | 0.990 | 0.991 | 0.961 | 0.966 |

TABLE 10

Color Chart DataColor Instrument Readings: Yellow and Green Color Blocks

|  |  | Block | | | | | | | |
|---|---|---|---|---|---|---|---|---|---|
|  |  | D. Yellow Column 3 ("D3") | | | | Yellow Column 3 ("Y3") | | Green Column 1 ("G1") | |
|  |  | Row | | | | | | | |
|  |  | a | b | c | d | a | b | c | d |
| DataColor | L | 83.21 | 84.66 | 90.77 | 91.88 | 76.70 | 84.50 | 88.10 | 91.06 |
|  | a | −12.43 | −11.04 | −4.12 | −2.53 | −23.13 | −13.86 | −8.70 | −4.44 |
|  | b | 56.59 | 52.71 | 23.90 | 16.40 | 46.53 | 33.38 | 23.97 | 15.29 |
|  | c | 57.94 | 53.85 | 24.25 | 16.59 | 51.96 | 36.14 | 25.50 | 15.92 |
|  | h | 102.39 | 101.83 | 99.77 | 98.78 | 116.43 | 112.54 | 109.94 | 106.18 |
| Converted | H | 57.0 | 55.3 | 50.4 | 48.2 | 74.5 | 67.0 | 62.4 | 56.3 |
|  | S | 0.557 | 0.512 | 0.234 | 0.165 | 0.498 | 0.321 | 0.220 | 0.141 |
|  | V | 0.854 | 0.875 | 0.936 | 0.940 | 0.781 | 0.850 | 0.880 | 0.914 |

TABLE 11

Color Chart DataColor Instrument Readings: Green Color Block

| | | Block | | | | | | | |
|---|---|---|---|---|---|---|---|---|---|
| | | Green Column 2 ("G2") | | | | Green Column 3 ("G3") | | | |
| | | Row | | | | | | | |
| | | a | b | c | d | a | b | c | d |
| DataColor | L | 69.37 | 80.54 | 85.21 | 90.36 | 66.38 | 78.94 | 85.04 | 89.91 |
| | a | −23.77 | −15.93 | −11.19 | −4.66 | −21.38 | −14.17 | −9.30 | −4.67 |
| | b | 29.38 | 22.81 | 18.05 | 11.07 | 16.12 | 13.06 | 10.61 | 8.53 |
| | c | 37.79 | 27.83 | 21.24 | 12.01 | 26.77 | 19.27 | 14.23 | 9.72 |
| | h | 128.97 | 124.93 | 121.79 | 112.82 | 142.98 | 137.33 | 131.22 | 118.68 |
| Converted | H | 92.7 | 84.7 | 79.5 | 65.2 | 120.0 | 106.9 | 96.0 | 75.8 |
| | S | 0.362 | 0.244 | 0.182 | 0.101 | 0.232 | 0.156 | 0.115 | 0.081 |
| | V | 0.706 | 0.813 | 0.855 | 0.899 | 0.672 | 0.794 | 0.851 | 0.895 |

Final Solution Testing: The Final Color Solutions were randomized and renumbered so that similar colors were not next to each other. Solutions were transferred to CLINITEK Novus® tubes and placed in racks for easier handling.

The Final Color Solution testing was performed by comparing the results from visual readings and Novus analysis. As stated above, all Final Color Solutions were tested on each of three (3) Novus instruments and the data was collected with the ASTM data collection software. Visual testing was completed by five (5) individuals who read the solutions independently. Each individual was given both the Final Color Solutions and the color chart. The layout of the color chart was explained (divided into the 5 CLINITEK Novus® color Blocks (Red, Orange, Dark Yellow, Yellow and Green)), and each individual was instructed to match the Final Color Solutions to a swatch on the color chart. Each individual read one Final Color Solution at a time in the order that the solutions were presented. As the result of each Final Color Solution was determined, an independent recorder tallied the results on the record form. The recorder also confirmed results with the reader to ensure the data was correct.

Data Analysis: The CLINITEK Novus® data files were processed through the UDAT data analysis program and the means and standard deviations (SD) data were calculated with a Microsoft Excel spreadsheet. The visual results were also transferred to a spreadsheet. A frequency table was generated to compare visual results to CLINITEK Novus®.

The goal of this testing was to define the degree of correlation between the CLINITEK Novus® and visual reads for the Final Color Solutions; therefore, there were no pass/fail criteria.

All three (3) CLINITEK Novus® instruments read the 20 Final Color Solutions the same. However, there were some variation between the individuals that performed the visual analysis. The comparison of the results from the CLINITEK Novus® instruments vs. the visual analysis is shown in Table 12. In this table, the color detected by the instruments is provided in the first column (labeled CLINITEK Novus® Results) and the results of the visual analysis is provided under the column labeled with the color (Red, Orange, Dark Yellow, Yellow, Green). As shown in the Table, the Final Color Solutions Red, Dark Yellow, and Green were detected 100% by both the instruments and individual readers. For the Orange samples, 3 of the 20 were labeled as Red with the visual analysis. For the Yellow samples, 1 was labeled as green by one visual reader.

TABLE 12

Frequency Table: CLINITEK Novus ® vs Visual

| Color | Visual Results | | | | | |
|---|---|---|---|---|---|---|
| CLINITEK Novus ® Results | Red | Orange | Dark Yellow | Yellow | Green | Grand Total |
| Red | 20 | 3 | | | | 23 |
| Orange | | 17 | | | | 17 |
| Dark Yellow | | | 20 | | | 20 |
| Yellow | | | | 19 | | 19 |
| Green | | | | 1 | 20 | 21 |
| Grand Total | 20 | 20 | 20 | 20 | 20 | 80 |
| % Exact Match | 100.0% | 85.0% | 100.0% | 95.0% | 100.0% | — |

Exact Agreement: 95%

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

EMBODIMENTS

The following list of embodiments is intended to complement, rather than displace or supersede, the previous descriptions.

Embodiment 1. A color chart comprising:
a surface material having one or more color swatches, wherein the color swatches comprise one or more layers of a dried water color pigment solution, wherein the water color pigment solution contains color pigment molecules.

Embodiment 2. The color chart of embodiment 1, wherein a color swatch having multiple layers of a dried water color pigment solution has a darker hue compared to a color swatch having fewer layers of the dried water color pigment solution.

Embodiment 3. The color chart of embodiment 1 or 2, wherein the one or more color swatches are arranged in one or more color sections.

Embodiment 4. The color chart of embodiment 3, wherein the one or more color sections comprise a red color section, an orange color section, a yellow color section, a green color section, or any combination thereof.

Embodiment 5. The color chart of embodiment 4, wherein the yellow color section comprises a dark yellow color section, a light yellow color section, or both a dark yellow color section and a light yellow color section.

Embodiment 6. The color chart of embodiment 4 or 5, wherein
a. the red color section comprises a hue from about 347.1 to about 360.0 or from about 0.0 to about 20.0;
b. the orange color section comprises a hue from about 24.1 to about 36.7;
c. the yellow color section comprises a hue from about 38.4 to about 57.0;
d. the green color section comprises a hue from about 74.5 to about 120.0; or
e. any combination of a-d.

Embodiment 7. The color chart of any one of the previous embodiments, wherein the color of the one or more color swatches correlates with a color of one or more water color pigment solutions.

Embodiment 8. The color chart of any one of the previous embodiments, wherein the water color pigment solution comprises a suspension of one or more water color pigments.

Embodiment 9. The color chart of embodiment 8, wherein the one or more water color pigments comprise orange, brilliant red, medium yellow, cobalt blue, raw umber, sap green, or any combination thereof.

Embodiment 10. The color chart of embodiment 8 or 9, wherein the one or more water color pigments comprises a combination of:
a) brilliant red and cobalt blue;
b) brilliant red and orange;
c) orange and medium yellow;
d) medium yellow and sap green; or
e) sap green and cobalt blue.

Embodiment 11. A water color pigment solution comprising:
a suspension of one or more water color pigments; and
urine or a solution that mimics urine.

Embodiment 12. The water color pigment solution of embodiment 11, wherein the one or more water color pigments comprise orange, brilliant red, medium yellow, cobalt blue, raw umber, sap green, or any combination thereof.

Embodiment 13. The water color pigment solution of embodiment 11 or 12, wherein the one or more water color pigments comprise a combination of:
a) brilliant red and cobalt blue;
b) brilliant red and orange;
c) orange and medium yellow;
d) medium yellow and sap green; or
e) sap green and cobalt blue.

Embodiment 14. The water color pigment solution of any one of embodiments 11-13, further comprising a preservative.

Embodiment 15. The water color pigment solution of embodiment 14, wherein the preservative is sodium azide.

Embodiment 16. A method of calibrating a reflectance-based diagnostic analyzer comprising:
inserting the color chart of any one of embodiments 1-10 or the water color pigment solutions of any one of embodiments 11-15 into the reflectance-based diagnostic analyzer, wherein the color chart or the water color pigment solutions have a known color;
obtaining reflectance values for the color chart or the water color pigment solutions; and
if the obtained reflectance values do not correspond to the known color of the color chart or the water color pigment solutions, calibrating the analyzer such that the reflectance values correspond to the known color of the color chart or the water color pigment solutions.

Embodiment 17. The method of embodiment 16, wherein the reflectance-based diagnostic analyzer is a portable diagnostic analyzer.

Embodiment 18. A kit comprising the color chart of any one of embodiments 1-10 or the water color pigment solutions of any one of embodiments 11-15 and instructions for using the color charts or water color pigment solutions.

Embodiment 19. The kit of embodiment 18, wherein the instructions explain to a user of the kit how to calibrate a reflectance-based diagnostic analyzer.

What is claimed:

1. A method of calibrating a reflectance-based diagnostic analyzer comprising:
inserting a color chart into the reflectance-based diagnostic analyzer, wherein the color chart comprises a surface material having one or more color swatches, wherein each color swatch comprises layers of a dried water color pigment solution providing a known color, wherein the water color pigment solution contains a suspension of water color pigment molecules, and wherein the color chart or the water color pigment solution has a known color;
obtaining reflectance values for the color chart or the water color pigment solution; and
when the obtained reflectance values do not correspond to the known color of the color chart or the water color pigment solution, calibrating the analyzer such that the reflectance values correspond to the known color of the color chart or the water color pigment solution.

2. The method of claim 1, wherein the reflectance-based diagnostic analyzer is a portable diagnostic analyzer.

3. The method of claim 1, wherein in the color chart, a color swatch having multiple layers of a dried water color pigment solution has a darker hue compared to a color swatch having fewer layers of the dried water color pigment solution.

4. The method of claim 1, wherein the one or more color swatches of the color chart is arranged in one or more color sections.

5. The method of claim 4, wherein the one or more color sections contains a red color section, an orange color section, a yellow color section, a green color section, or any combination thereof.

6. The method of claim 5, wherein the yellow color section has a dark yellow color section, a light yellow color section, or both a dark yellow color section and a light yellow color section.

7. The method of claim 5, wherein:
   a. the red color section has a hue in a range of from about 347.1 to about 360.0 or in a range of from about 0.0 to about 20.0;
   b. the orange color section has a hue in a range of from about 24.1 to about 36.7;
   c. the yellow color section has a hue in a range of from about 38.4 to about 57.0;
   d. the green color section has a hue in a range of from about 74.5 to about 120.0; or
   e. any combination of a-d.

8. The method of claim 1, wherein the color of the one or more color swatches of the color chart correlates with a color of one or more water color pigment solutions.

9. The method of claim 1, wherein the water color pigment solution of the color chart comprises a suspension of one or more water color pigments.

10. The method of claim 9, wherein the one or more water color pigments comprise at least one of orange, brilliant red, medium yellow, cobalt blue, raw umber, sap green, or any combination thereof.

11. The method of claim 9, wherein the one or more water color pigments comprises a combination of:
   a) brilliant red and cobalt blue;
   b) brilliant red and orange;
   c) orange and medium yellow;
   d) medium yellow and sap green; or
   e) sap green and cobalt blue.

\* \* \* \* \*